United States Patent
Matsumoto et al.

(10) Patent No.: US 12,115,031 B2
(45) Date of Patent: Oct. 15, 2024

(54) DENTAL MILL BLANK AND DENTAL PROSTHESIS

(71) Applicant: KURARAY NORITAKE DENTAL INC., Kurashiki (JP)

(72) Inventors: Atsushi Matsumoto, Aichi (JP); Hiroyuki Sakamoto, Aichi (JP); Shinichiro Kato, Aichi (JP); Yoshihisa Ito, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 278 days.

(21) Appl. No.: 17/418,004

(22) PCT Filed: Dec. 25, 2019

(86) PCT No.: PCT/JP2019/050893
§ 371 (c)(1),
(2) Date: Jun. 24, 2021

(87) PCT Pub. No.: WO2020/138197
PCT Pub. Date: Jul. 2, 2020

(65) Prior Publication Data
US 2022/0087794 A1 Mar. 24, 2022

(30) Foreign Application Priority Data

Dec. 26, 2018 (JP) ................................. 2018-243474
Jun. 27, 2019 (JP) ................................. 2019-120129

(51) Int. Cl.
A61C 13/00 (2006.01)
A61C 13/083 (2006.01)
(Continued)

(52) U.S. Cl.
CPC ........ *A61C 13/0022* (2013.01); *A61C 13/083* (2013.01); *A61C 13/09* (2013.01); *A61C 5/70* (2017.02)

(58) Field of Classification Search
None
See application file for complete search history.

(56) References Cited

U.S. PATENT DOCUMENTS

| | | | |
|---|---|---|---|
| 2006/0008774 A1 | 1/2006 | Orth et al. | |
| 2011/0104643 A1* | 5/2011 | Giordano | ........... A61C 13/0022 264/16 |

(Continued)

FOREIGN PATENT DOCUMENTS

| | | |
|---|---|---|
| EP | 0 850 601 A2 | 7/1998 |
| JP | 2008-539920 A | 11/2008 |

(Continued)

OTHER PUBLICATIONS

International Search Report issued on Feb. 10, 2020 in PCT/JP2019/050893 filed on Dec. 25, 2019, 2 pages.

*Primary Examiner* — Elizabeth Collister
(74) *Attorney, Agent, or Firm* — Oblon, McClelland, Maier & Neustadt, L.L.P.

(57) ABSTRACT

A mill blank may have a multilayer structure and desirable aesthetics. Such dental mill blanks may include a mill blank portion having a layered structure of two or more layers, and in which the layered structure includes an enamel layer and a core layer, the core layer comprising a first portion that is substantially a frustum, the frustum having a side face forming a part of an interface between the enamel layer and the core layer.

14 Claims, 16 Drawing Sheets

(51) Int. Cl.
*A61C 13/09* (2006.01)
*A61C 5/70* (2017.01)

(56) References Cited

U.S. PATENT DOCUMENTS

| | | | |
|---|---|---|---|
| 2013/0069264 A1* | 3/2013 | Giordano | A61C 13/0018 264/16 |
| 2014/0255875 A1* | 9/2014 | Saliger | A61C 5/70 433/223 |
| 2014/0356815 A1* | 12/2014 | Spalt | G06F 30/00 433/213 |
| 2018/0002235 A1* | 1/2018 | Ito | A61C 8/0012 |
| 2018/0002265 A1* | 1/2018 | Wright | C07C 41/34 |

FOREIGN PATENT DOCUMENTS

| | | |
|---|---|---|
| JP | 2014-534018 A | 12/2014 |
| JP | 2016-535610 A | 11/2016 |
| WO | WO 2015/051095 A1 | 4/2015 |
| WO | WO 2017/114776 A1 | 7/2017 |

* cited by examiner

DENTAL MILL BLANK AND DENTAL PROSTHESIS

CROSS-REFERENCE TO RELATED APPLICATIONS

The present application is the national stage of international application PCT/JP2019/050893, filed on Dec. 25, 2019, and claims the benefit of the filing dates of Japanese Appl. No. 2019-120129 and 2018-243474, respectively filed on Jun. 27, 2019, and Dec. 26, 2018.

TECHNICAL FIELD

The present invention relates to a dental mill blank and a dental prosthesis.

BACKGROUND ART

For years, metal has been used for a range of dental products, including, for example, prostheses (such as veneer crowns, dental caps, crowns, and post crowns), orthodontic products, and products for dental implants. However, metals lack aesthetic quality because of the colors that are distinctively different from the color of natural teeth, and can cause allergic reaction when released from these products. These issues involving the use of metal have been addressed by dental products that use ceramic materials such as aluminum oxide (alumina) and zirconium oxide (zirconia) as alternative materials of metal. Comparatively, zirconia, in particular, has desirable strength and more appealing aesthetics, and this, combined with the currently declining price of zirconia, has created a high demand for this material.

For improved oral aesthetics, a dental product must match the appearance of natural teeth. It is, however, difficult to reproduce the appearance of natural teeth (particularly, transparency and gloss (luster)) with zirconia (sintered body) alone.

Patent Literature 1 discloses a resin-based dental mill blank having layers with curved surfaces.

Patent Literature 2 discloses a blank configured from a dentin-color, low-translucency material forming inside of a block, and an enamel-equivalent, high-translucency material surrounding the low-translucency material.

CITATION LIST

Patent Literature

Patent Literature 1: JP 2016-535610 T
Patent Literature 2: JP 2014-534018 T

SUMMARY OF INVENTION

Technical Problem

A prosthesis fabricated from a mill blank produced by the method of Patent Literature 1 has a structure that looks like kamaboko, and the gradation occurs only from front to back, and vice versa (as a front tooth). Because of this structure, the prosthesis, when used as a front tooth in particular, has low translucency inside the tooth at the left and right edges, and is unable to reproduce the transparency and the shade of the incisal region. This makes the prosthesis of the related art inferior in terms of aesthetics. The prosthesis is also problematic in terms of strength and durability because it is resin-based. The method of this related art also lacks convenience because it involves joining by co-extrusion, sequential extrusion, sequential pressing, or additive buildup.

In Patent Literature 2, the blank material is described as being ceramic or acrylate. However, this related art does not describe a specific method of production, and does not include specific names of ceramics. There is also no description of processes such as calcining and firing.

Accordingly, it is an object of the present invention to provide a mill blank and dental prosthesis having a multilayer structure and desirable aesthetics.

Solution to Problem

The present inventors conducted intensive studies to find a solution to the foregoing problems, and found that the problems can be solved by employing a specific multilayer structure. The present inventors completed the present invention after further studies based on this finding.

Specifically, the present invention includes the following.

[1] A dental mill blank that comprises a mill blank portion having a layered structure of two or more layers, and in which the layered structure comprises an enamel layer and a core layer,
the core layer comprising a first portion that is substantially a frustum,
the frustum having a side face forming a part of an interface between the enamel layer and the core layer.

[2] The dental mill blank according to [1], wherein an angle $\theta 1$ created by the side face of the frustum and an imaginary line orthogonal to a relatively wider base B of the frustum falls in a range of 0° to 80° (excluding 0°) on an imaginary plane orthogonal to the base B.

[3] The dental mill blank according to [1] or [2], wherein the frustum has a circular or elliptical base.

[4] The dental mill blank according to any one of [1] to [3], wherein the core layer further comprises a second portion joined to the first portion at a relatively wider base B of the frustum.

[5] The dental mill blank according to [4], wherein the second portion has a pedestal face that is in contact with the base B of the first portion, and the pedestal face forms a part of the interface around a region contacting the first portion.

[6] The dental mill blank according to [5], wherein the second portion is a portion that is a) substantially a frustum having the pedestal face as a relatively narrower base C, b) substantially a column having the pedestal face as a base C, or c) a combination of a portion that is substantially a frustum having the pedestal face as a relatively narrower base C, and a portion that is substantially a column joined to a relatively wider base of the frustum.

[7] The dental mill blank according to [4], wherein the second portion is a portion that is d) substantially a frustum having a relatively narrower base C representing a surface identical in size and position to the base B, e) substantially a column having a base C representing a surface identical in size and position to the base B, or f) a combination of a portion that is substantially a frustum having a relatively narrower base C representing a surface identical in size and position to the base B of the first portion, and a portion that is substantially a column having a base E representing a surface identical in size and position to a relatively wider base D of the frustum.

[8] The dental mill blank according to [6], wherein the second portion is a cylindrical portion having the pedestal face as a base C.
[9] The dental mill blank according to [7], wherein the second portion is a cylindrical portion having a base C representing a surface identical in size and position to the base B.
[10] The dental mill blank according to any one of [4] to [9], wherein the second portion comprises a plurality of layers of different shades.
[11] The dental mill blank according to [10], wherein the second portion comprises an upper layer and a lower layer that are different in shade, the upper layer and the lower layer having a shade difference ΔE of 0.5 or more as calculated by the following formula, $$\Delta E = \sqrt{(L10-L9)^2+(a10-a9)^2+(b10-b9)^2}$$ [Math. 1]

where (L9,a9,b9) represent (L*,a*,b*) of the upper layer of the second portion, and (L10,a10,b10) represent (L*,a*,b*) of the lower layer of the second portion.
[12] The dental mill blank according to any one of [1] to [11], wherein the first portion has chromaticity with L*=62 to 86, a*=−2 to 7, and b*=4 to 27 in the L*a*b* color system.
[13] The dental mill blank according to any one of [1] to [12], wherein the core layer further comprises a third portion joined to the first portion at a relatively narrower base A of the frustum forming the first portion, and/or the base A of the core layer forms a part of the interface between the enamel layer and the core layer.
[14] The dental mill blank according to any one of [1] to [13], wherein the mill blank portion is a zirconia pre-sintered body.
[15] A dental prosthesis comprising a dental mill blank of any one of [1] to [14].

Advantageous Effects of Invention

The present invention can provide a dental mill blank and dental prosthesis having a multilayer structure and desirable aesthetics. Specifically, the present invention can provide a dental mill blank and dental prosthesis having a multilayer structure close in shade and translucency to natural teeth. The present invention can also provide a method that enables easy production of a dental mill blank and a dental prosthesis. The present invention can also provide a mill blank and dental prosthesis having a multilayer structure and desirable strength and durability, and methods for producing such a mill blank and a dental prosthesis.

DESCRIPTION OF EMBODIMENTS

A feature of the present invention lies in a mill blank that comprises a mill blank portion having a layered structure of two or more layers, and in which the layered structure comprises an enamel layer and a core layer, the core layer comprising a first portion that is substantially a frustum, the frustum having a side face forming a part of an interface between the enamel layer and the core layer.

Mill Blank Portion

Figure 1A:
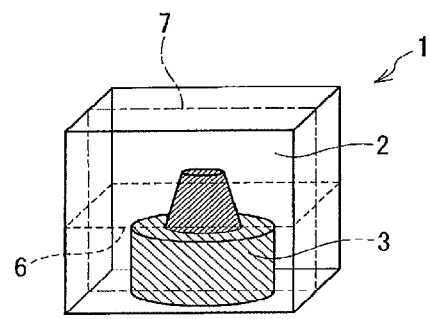
FIG. 1A is a schematic diagram representing an exemplary embodiment of a mill blank portion according to the present invention.

A mill blank portion (1) of the present invention has a layered structure of two or more layers including an enamel layer (2) and a core layer (3). FIG. 1A represents an example of the mill blank portion (1).

Figure 1B:
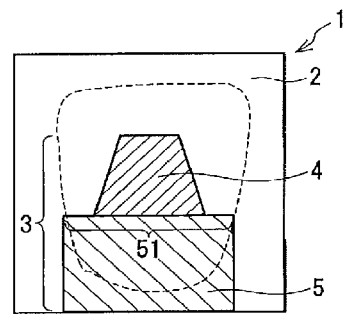
FIG. 1B is a cross sectional view of a mill blank portion according to the present invention at a second imaginary cutting plane.
Figure 1C:
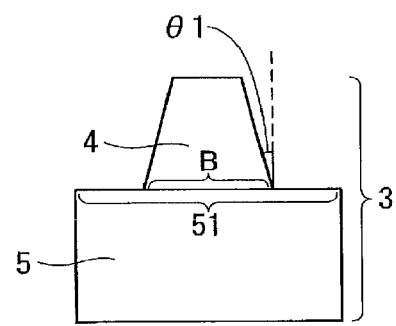
FIG. 1C is a cross sectional view of a core layer of a mill blank portion according to the present invention at a second imaginary cutting plane.

The core layer (3) is a layer that has the property to mask the shade of an abutment tooth so as to prevent the shade of the abutment tooth from appearing on the surface of the mill blank portion (1), and needs to be formed inside the enamel layer (2). The core layer (3) comprises a first portion (4) that is substantially a frustum, and the frustum has a side face forming a part of the interface between the enamel layer (2) and the core layer (3). With this construction, the first portion (4) will not be exposed by itself to dental cap surfaces of a dental prosthesis after milling, regardless of whether the dental cap is seen from the front or sides, and provides a structure that more resembles a natural tooth (dentin is inside the enamel), producing shades similar to the shades of a natural tooth. The dotted line in FIG. 1B indicates the frontal position of a dental cap of when the mill blank portion (1) is milled into a prosthesis for front tooth. The dotted line in FIG. 1E indicates the lateral position of a dental cap of when the mill blank portion (1) is milled into a prosthesis for front tooth. Similarly, the dotted line in FIG. 1F indicates the frontal position of a dental cap of when the mill blank portion (1) is milled into a prosthesis for molar, and the dotted line in FIG. 1G indicates the lateral position of a dental cap of when the mill blank portion (1) is milled into a prosthesis for molar. In the mill blank portion (1), the first portion (4) of the core layer (3) has a height that is determined as desired to look more similar to the dentin of a natural tooth. The height of the first portion (4) is preferably 20 to 90%, more preferably 30 to 80%, even more preferably 35 to 65% of the height of the core layer (3), though it is not particularly limited. The lower base of the core layer (3) may be covered with the enamel layer (2), or may be exposed at a surface of the mill blank portion (1).

The preferred shapes of the core layer (3) are described below.

Figure 4A:
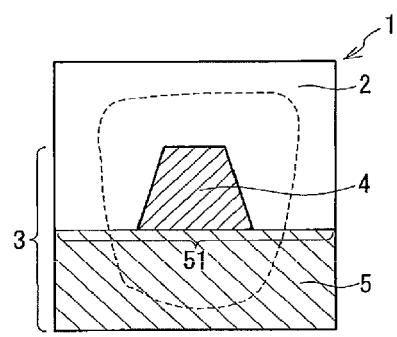
FIG. 4A is a cross sectional view of a mill blank portion according to another embodiment of the present invention at a second imaginary cutting plane.
Figure 4B:
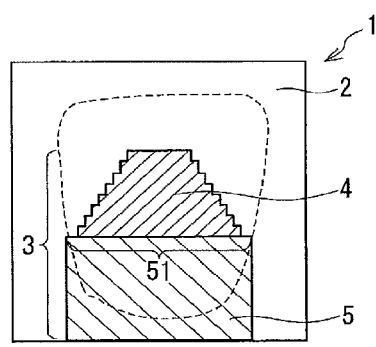
FIG. 4B is a cross sectional view of a mill blank portion according to another embodiment of the present invention at a second imaginary cutting plane.
Figure 4C:
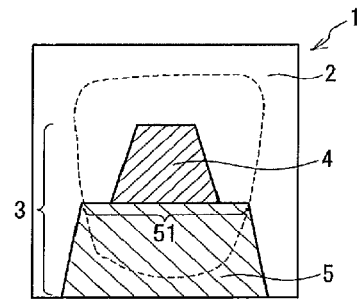
FIG. 4C is a cross sectional view of a mill blank portion according to another embodiment of the present invention at a second imaginary cutting plane.
Figure 4D:
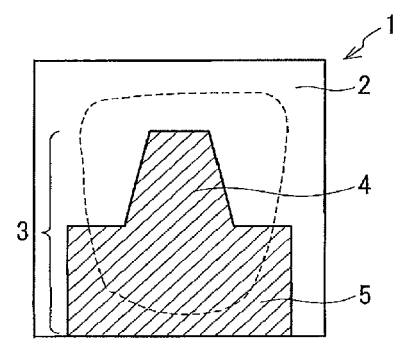
FIG. 4D is a cross sectional view of a mill blank portion according to another embodiment of the present invention at a second imaginary cutting plane.
Figure 4E:
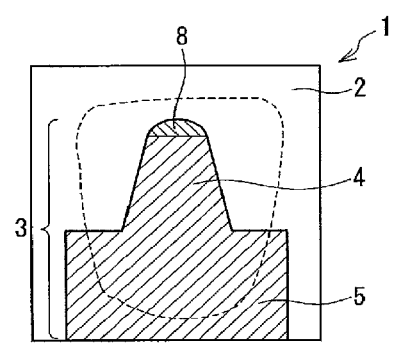
FIG. 4E is a cross sectional view of a mill blank portion according to another embodiment of the present invention at a second imaginary cutting plane.

The core layer (3) comprises a first portion that is substantially a frustum. Here, "substantially a frustum" refers to a shape that can be recognized as a frustum, including a pyramidal frustum and a circular frustum. For example, "frustum" in the present invention includes shapes with finely stepped side faces (for example, FIG. 4B), shapes with a rounded first portion (4) (for example, FIG. 4O, FIG. 4Q), and shapes having a depression in a relatively narrower base A of first portion (4) (for example, FIG. 4J, FIG. 4S), provided that the angle θ1 (see FIG. 1C) created by the side face of the frustum and an imaginary line orthogonal to a relatively wider base B of the frustum falls in a range of 0° to 80° (excluding 0°) on an imaginary plane orthogonal to the base B (for example, second imaginary cutting plane (7) in FIG. 1A). The angle θ1 is preferably 10° or more, more preferably 15° or more, even more preferably 20° or more because the core layer, in a side view, can be less exposed to the front of a prosthetic dental cap after milling when the angle θ1 is confined in these ranges. The angle θ1 is preferably 50° or less, more preferably 40° or less, even more preferably 30° or less, because the core layer, in a side view, can have a sufficiently large area at the front of a prosthetic dental cap after milling when the angle θ1 is confined in these ranges. With these shapes of core layer (3), the dental prosthesis can more closely resemble the structure of a natural tooth.

Figure 3A:
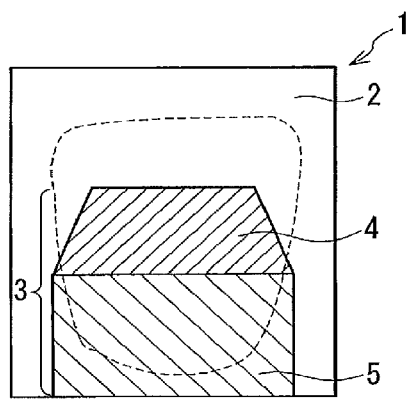
FIG. 3A is a cross sectional view of a mill blank portion according to the present invention at a second imaginary cutting plane.
Figure 3B:
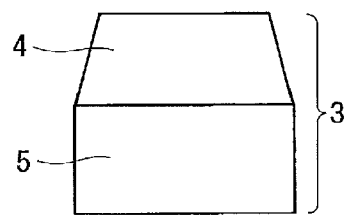
FIG. 3B is a cross sectional view of a core layer of a mill blank portion according to the present invention at a second imaginary cutting plane.
Figure 3C:
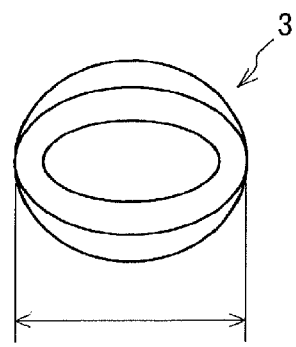
FIG. 3C is a cross sectional view of a core layer of a mill blank portion according to the present invention at a first imaginary cutting plane.
Figure 3D:
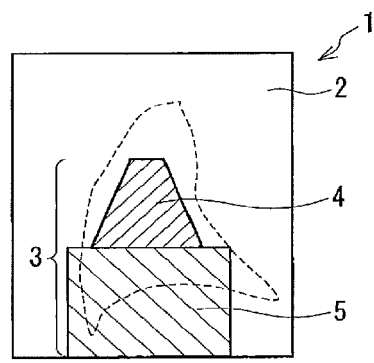
FIG. 3D is a cross sectional view of a mill blank portion according to the present invention at a second imaginary cutting plane.
Figure 3E:
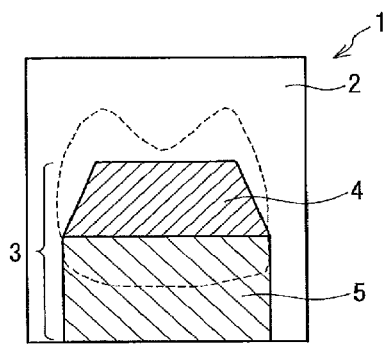
FIG. 3E is a cross sectional view of a mill blank portion according to the present invention at a second imaginary cutting plane.
Figure 3F:
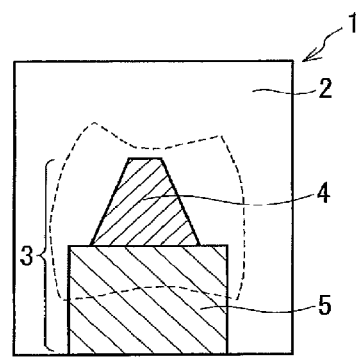
FIG. 3F is a cross sectional view of a mill blank portion according to the present invention at a second imaginary cutting plane.

Preferably, the frustum has a circular or elliptical base. The frustum is preferably a circular frustum or an elliptical frustum. The frustum is more preferably a circular frustum because it provides superior aesthetics for the dental cap in front and side views. A certain preferred embodiment of the present invention is a dental mill blank that comprises, as shown in FIG. 3A to FIG. 3F, a mill blank portion (1) having a layered structure of two or more layers, and in which the layered structure includes an enamel layer (2) and a core layer (3), the core layer (3) comprising a first portion (4) that is an elliptical frustum, and the frustum having a side face forming a part of the interface between the enamel layer (2) and the core layer (3). When the first portion (4) is an elliptical frustum as shown in FIG. 3B and FIG. 3C, a dental prosthesis for front tooth that shows a color similar to the color of natural teeth can be provided by milling the dental mill blank as indicated by dotted lines in FIG. 3A (the dotted line represents the front surface of a prosthetic dental cap for front tooth) and FIG. 3D (the dotted line represents a side surface of a prosthetic dental cap for front tooth).

Figure 1D:
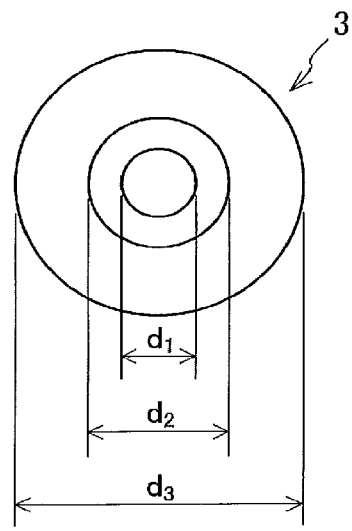
FIG. 1D is a cross sectional view of a core layer of a mill blank portion according to the present invention at a first imaginary cutting plane.
Figure 1E:
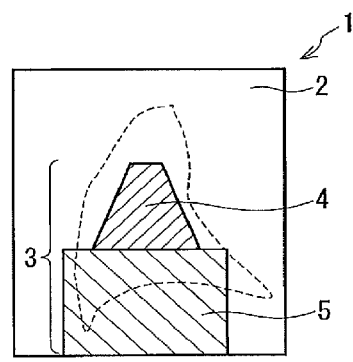
FIG. 1E is a cross sectional view of a mill blank portion according to the present invention at a second imaginary cutting plane.
Figure 1F:
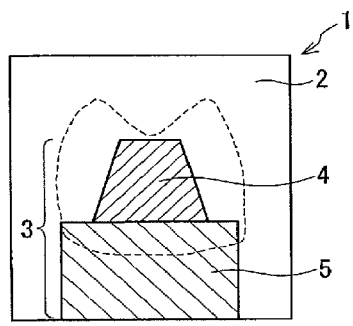
FIG. 1F is a cross sectional view of a mill blank portion according to the present invention at a second imaginary cutting plane.
Figure 1G:
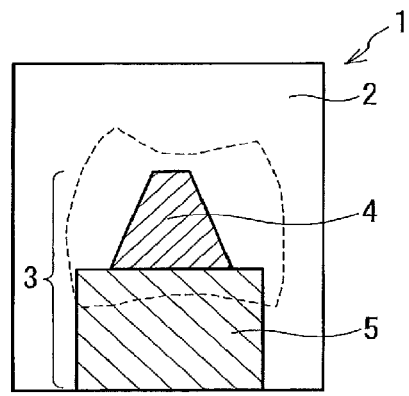
FIG. 1G is a cross sectional view of a mill blank portion according to the present invention at a second imaginary cutting plane.

A certain preferred embodiment of the present invention is a dental mill blank in which the core layer (3) in any of the embodiments above further comprises a second portion (5) joined to the first portion (4) at a relatively wider base B of the frustum. In an example of such an embodiment, the first portion (4) has a base B having a relatively wider area ($\pi(d_2/2)^2$) than base A ($\pi(d_1/2)^2$), and the dental mill blank further comprises a second portion (5) joined to the first portion (4) at the base B, as shown in FIG. 1D representing a top view of FIG. 1C as seen from above the first portion (4).

Preferably, the second portion (5) has a pedestal face (51) that is in contact with the base B of the first portion (4), and the pedestal face (51) forms a part of the interface between the enamel layer (2) and the core layer (3) around a region contacting the first portion (4). In other words, the core layer (3) may be shaped to include a step formed by the first portion (4) and the second portion (5), as shown in FIG. 1C. The shape of the second portion (5) is not particularly limited, as long as the present invention can produce its effects. It is, however, preferable that the second portion (5) be shaped to include bases and a side face, and that the side face have a portion perpendicular to the bases. In the present invention, the second portion (5) preferably has a pedestal face (51) that is larger in area than the base B of the first portion (4).

Figure 4F:
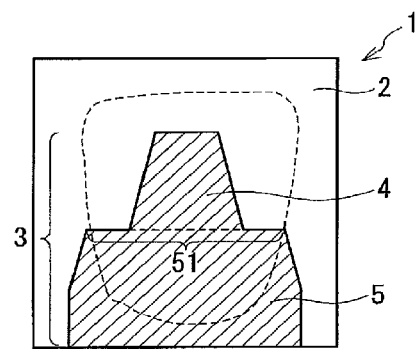
FIG. 4F is a cross sectional view of a mill blank portion according to another embodiment of the present invention at a second imaginary cutting plane.
Figure 4G:
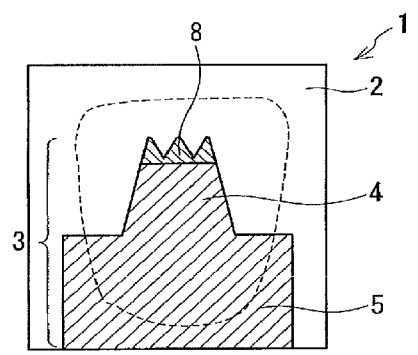
FIG. 4G is a cross sectional view of a mill blank portion according to another embodiment of the present invention at a second imaginary cutting plane.
Figure 4H:
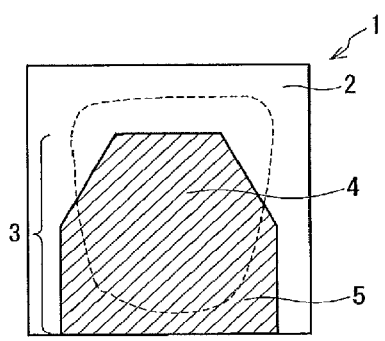
FIG. 4H is a cross sectional view of a mill blank portion according to another embodiment of the present invention at a second imaginary cutting plane.
Figure 4I:
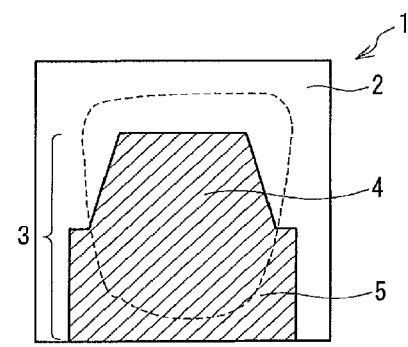
FIG. 4I is a cross sectional view of a mill blank portion according to another embodiment of the present invention at a second imaginary cutting plane.
Figure 4J:
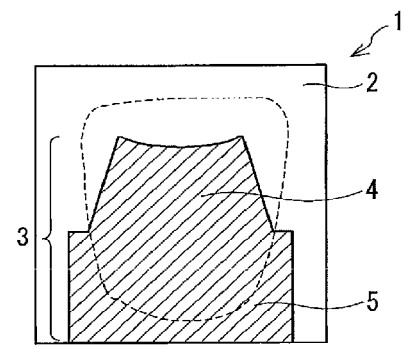
FIG. 4J is a cross sectional view of a mill blank portion according to another embodiment of the present invention at a second imaginary cutting plane.
Figure 4K:
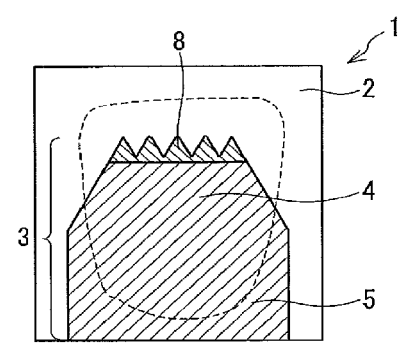
FIG. 4K is a cross sectional view of a mill blank portion according to another embodiment of the present invention at a second imaginary cutting plane.
Figure 4L:
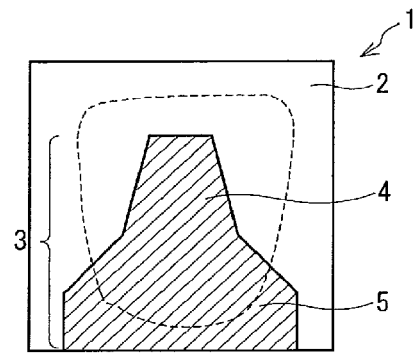
FIG. 4L is a cross sectional view of a mill blank portion according to another embodiment of the present invention at a second imaginary cutting plane.
Figure 4M:
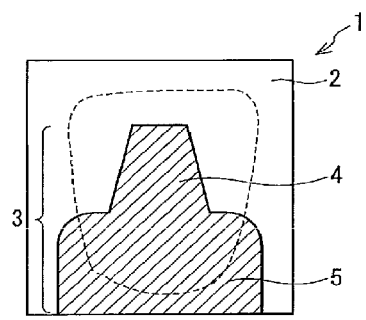
FIG. 4M is a cross sectional view of a mill blank portion according to another embodiment of the present invention at a second imaginary cutting plane.
Figure 4N:
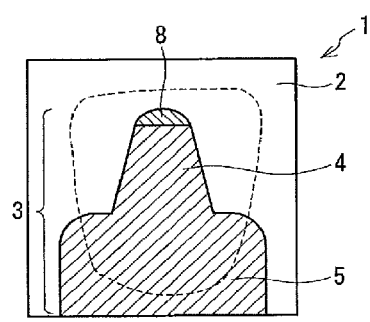
FIG. 4N is a cross sectional view of a mill blank portion according to another embodiment of the present invention at a second imaginary cutting plane.
Figure 4O:
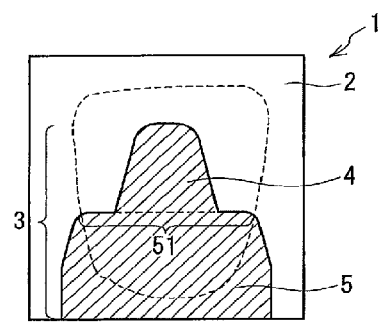
FIG. 4O is a cross sectional view of a mill blank portion according to another embodiment of the present invention at a second imaginary cutting plane.
Figure 4P:
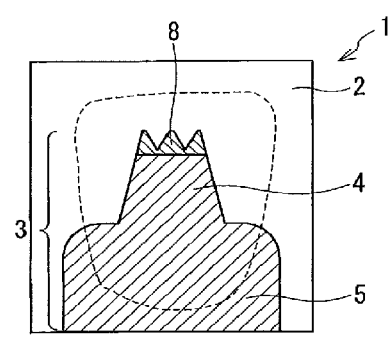
FIG. 4P is a cross sectional view of a mill blank portion according to another embodiment of the present invention at a second imaginary cutting plane.
Figure 4Q:
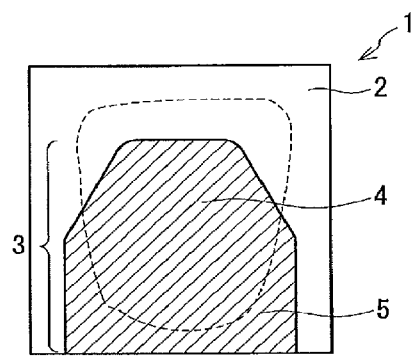
FIG. 4Q is a cross sectional view of a mill blank portion according to another embodiment of the present invention at a second imaginary cutting plane.
Figure 4R:
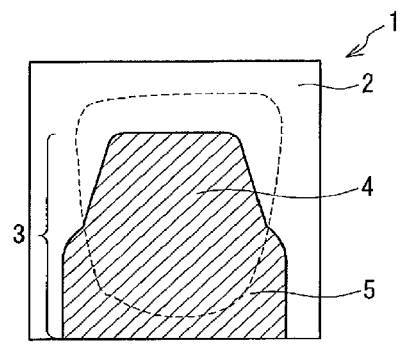
FIG. 4R is a cross sectional view of a mill blank portion according to another embodiment of the present invention at a second imaginary cutting plane.
Figure 4S:
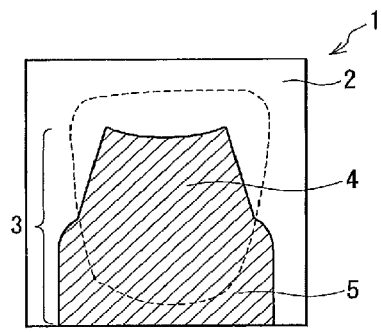
FIG. 4S is a cross sectional view of a mill blank portion according to another embodiment of the present invention at a second imaginary cutting plane.
Figure 4T:
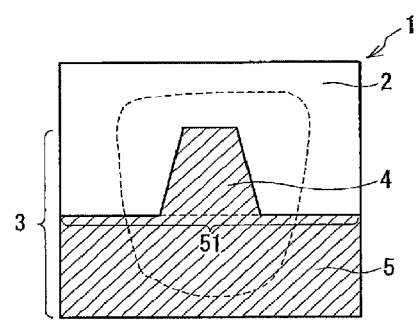
FIG. 4T is a cross sectional view of a mill blank portion according to another embodiment of the present invention at a second imaginary cutting plane.
Figure 4U:
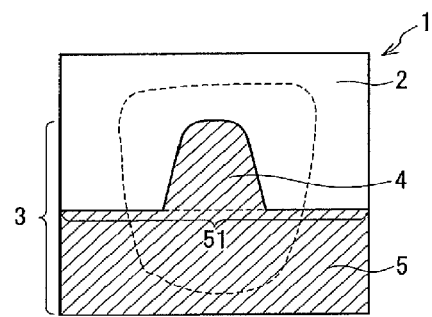
FIG. 4U is a cross sectional view of a mill blank portion according to another embodiment of the present invention at a second imaginary cutting plane.

In view of reproducing the transparency and shade of incisal edge portion and providing superior aesthetics as a dental prosthesis for front tooth, a certain preferred embodiment is a dental mill blank in which the second portion (5) is a portion that is a) substantially a frustum having the pedestal face (51) as a relatively narrower base C (for example, FIG. 4C), b) substantially a column (prism- or cylinder-shaped) having the pedestal face (51) as a base C (for example, FIG. 1B, FIG. 3D, FIG. 4A, FIG. 4B, FIG. 4T, FIG. 4U, FIG. 4V), or c) a combination of a portion that is substantially a frustum having the pedestal face (51) as a relatively narrower base C, and a portion that is substantially a column joined to a relatively wider base of the frustum (for example, FIG. 4F, FIG. 4O). In view of providing even superior aesthetics by more appropriately reproducing the transparency and shade of incisal edge portion, the second portion (5) is more preferably a portion that is b) substantially a column having the pedestal face (51) as a base C, or c) a combination of a portion that is substantially a frustum having the pedestal face (51) as a relatively narrower base C, and a portion that is substantially a column joined to a relatively wider base of the frustum, even more preferably a cylindrical portion having the pedestal face (51) as a base C. Examples of the prism shape include a quadrangular prism and a hexagonal prism. Examples of the cylinder shape include a cylinder and an elliptical cylinder. As used herein, "substantially a column" includes not only columns but, for example, shapes having round corners (for example, FIG. 4M, FIG. 4N, FIG. 4P, FIG. 4R, FIG. 4S), to the extent that the present invention can produce its effects. For example, in the dental mill blank of FIG. 1B, the second portion (5) has a height of preferably 4 mm or more, more preferably 5 mm or more, even more preferably 6 mm or more. The second portion (5) has a height of preferably 12 mm or less, more preferably 11 mm or less, even more preferably 10 mm or less. In the dental mill blank of FIG. 1B, the first portion (4) has a height of preferably 3 mm or more, more preferably 3.5 mm or more, even more preferably 4 mm or more. The first portion (4) has a height of preferably 10 m or less, more preferably 9.5 mm or less, even more preferably 8 mm or less. The first portion (4) and the second portion (5) have a height ratio of preferably 1:0.3 to 1:2 as a ratio of the height of first portion (4) to the height of second portion (5).

Figure 2A:
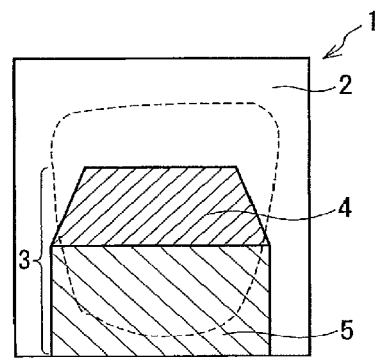
FIG. 2A is a cross sectional view of a mill blank portion according to the present invention at a second imaginary cutting plane.
Figure 2B:
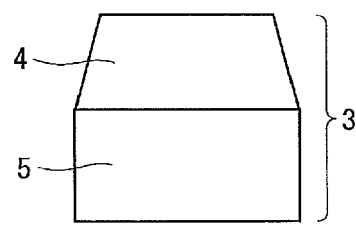
FIG. 2B is a cross sectional view of a core layer of a mill blank portion according to the present invention at a second imaginary cutting plane.
Figure 2C:
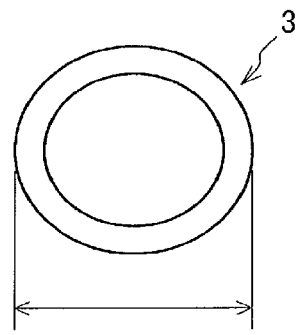
FIG. 2C is a cross sectional view of a core layer of a mill blank portion according to the present invention at a first imaginary cutting plane.
Figure 2D:
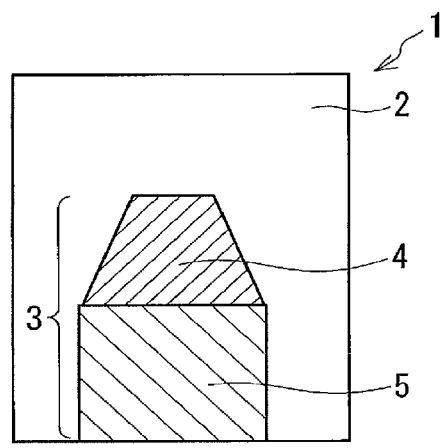
FIG. 2D is a cross sectional view of a mill blank portion according to the present invention at a second imaginary cutting plane.
Figure 2E:
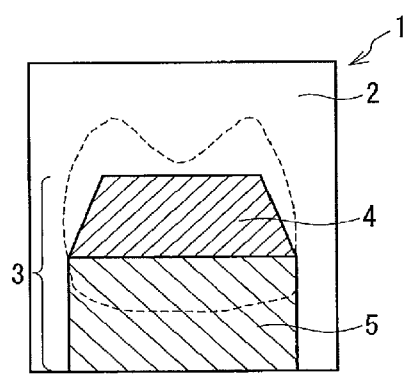
FIG. 2E is a cross sectional view of a mill blank portion according to the present invention at a second imaginary cutting plane.
Figure 2F:
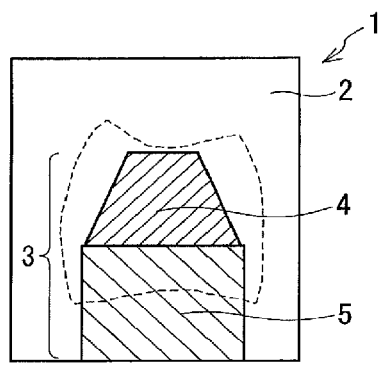
FIG. 2F is a cross sectional view of a mill blank portion according to the present invention at a second imaginary cutting plane.

In other preferred embodiments, the core layer (3) may be shaped so that the first portion (4) and the second portion (5) do not have a step, as shown in FIG. 2A. For example, in view of even superior aesthetics as a dental prosthesis for molar, a certain preferred embodiment is a dental mill blank in which the second portion (5) is a portion that is d) substantially a frustum having a relatively narrower base C representing a surface identical in size and position to the base B of the first portion (4), e) substantially a column having a base C representing a surface identical in size and position to the base B of the first portion (4) (for example, FIG. 4H, FIG. 4K, FIG. 4Q), or f) a combination of a portion that is substantially a frustum having a relatively narrower base C representing a surface identical in size and position to the base B of the first portion (4), and a portion that is substantially a column having a base E representing a surface identical in size and position to a relatively wider base D of the frustum (for example, FIG. 4L). In view of providing even superior aesthetics by reducing the area of enamel layer and providing a sufficient area that corresponds to dentin in a front view of a dental cap as a dental prosthesis for molar, the second portion (5) is more preferably a portion that is e) substantially a column having a base C representing a surface identical in size and position to the base B of the first portion (4), or f) a combination of a portion that is substantially a frustum having a relatively narrower base C representing a surface identical in size and position to the base B of the first portion (4), and a portion that is substantially a column having a base E representing a surface identical in size and position to a relatively wider base D of the frustum. For example, when the core layer (3) has the shape represented by FIG. 2B and FIG. 2C, a dental prosthesis for molar that shows a color similar to the color of natural teeth can be provided by milling the dental mill blank as indicated by dotted lines in FIG. 2E (the dotted line represents the front surface of a prosthetic dental cap for molar) and FIG. 2F (the dotted line represents a side surface of a prosthetic dental cap for molar).

Another preferred embodiment is a dental mill blank in which the core layer (3) in any of the embodiments above further comprises a third portion (8) joined to the first portion (4) at a relatively narrower base A of the frustum forming the first portion (4), and/or the base A of the core layer (3) forms a part of the interface between the enamel layer (2) and the core layer (3). The shape of the third portion (8) is not particularly limited, as long as the present invention can produce its effects. The third portion (8) may have a protruding shape (for example, FIG. 4E, FIG. 4N, FIG. 4V), or a shape with irregularities (for example, FIG. 4G, FIG. 4P).

Figure 4V:
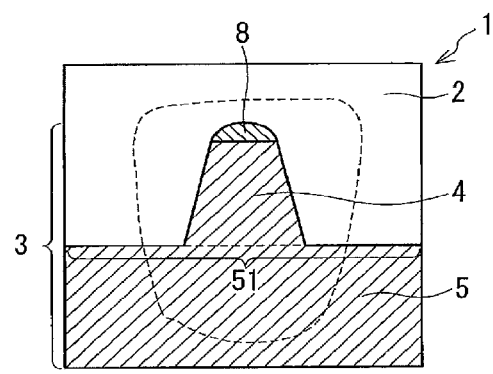
FIG. 4V is a cross sectional view of a mill blank portion according to another embodiment of the present invention at a second imaginary cutting plane.

In certain preferred embodiments of the present invention, any of the foregoing embodiments including the second portion (5) may be such that the first portion (4) and the second portion (5) have the same shade (for example, FIG. 4D to FIG. 4V).

In other preferred embodiments of the present invention, any of the foregoing embodiments including the second portion (5) may be such that the first portion (4) and the second portion (5) have different shades. In view of providing even superior aesthetics by preventing overly strong color development from inside that makes the dental mill blank unnaturally dark as a dental cap, the first portion (4) preferably has a shade that falls between the shade of the enamel layer (2) and the shade of the second portion (5) corresponding to dentin. With the first portion (4) having such a shade, the dental prosthesis can have a shade even closer to the shade of natural teeth with the moderately reduced color development from inside.

Figure 4W:
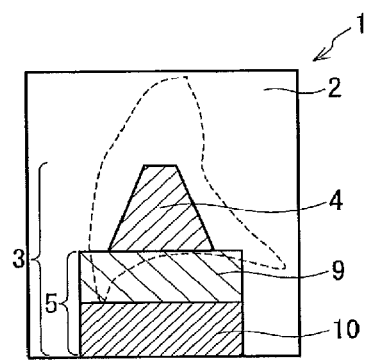
FIG. 4W is a cross sectional view of a mill blank portion according to another embodiment of the present invention at a second imaginary cutting plane.
Figure 4X:
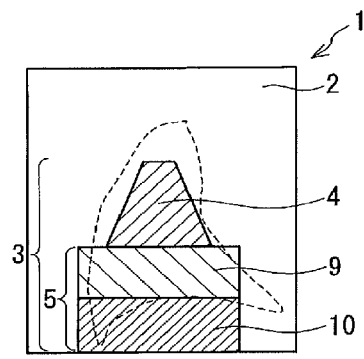
FIG. 4X is a cross sectional view of a mill blank portion according to another embodiment of the present invention at a second imaginary cutting plane.
Figure 4Y:
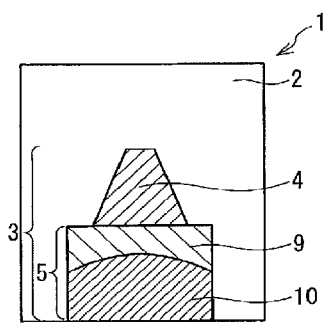
FIG. 4Y is a cross sectional view of a mill blank portion according to another embodiment of the present invention at a second imaginary cutting plane.
Figure 4Z:
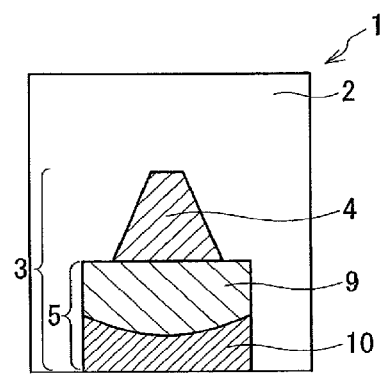
FIG. 4Z is a cross sectional view of a mill blank portion according to another embodiment of the present invention at a second imaginary cutting plane.

In other preferred embodiments, any of the foregoing embodiments including the second portion (5) may be such that the second portion (5) comprises a plurality of layers of difference shades. The shape of the boundary between the layers is not particularly limited, as long as the present invention can produce its effects, and may be parallel to the base (FIG. 4W, FIG. 4X), or may be convex (FIG. 4Y) or concave (FIG. 4Z). The number of layers in the second portion (5) is not particularly limited, and the second portion (5) may have two layers or three layers. With the second portion (5) having a plurality of layers of different shades, the same mill blank can be used to make dental caps of different shades by changing the position of the dental cap as desired when milling the mill blank. For example, when making a pale-shaded prosthesis for front tooth, the mill blank is milled as indicated by the dotted line in FIG. 4W (the dotted line represents a side surface of a prosthetic dental cap for front tooth). When making a dark-shaded prosthesis for front tooth, the mill blank is milled as indicated by the dotted line in FIG. 4X (the dotted line represents a side surface of a prosthetic dental cap for front tooth).

The shape of a mill blank of the present invention is not particularly limited, as long as a jig is attachable. For example, in any of the embodiments above, the mill blank may have a prism shape, and the shape is preferably a quadrangular prism in view of production, A preferred embodiment of the shade and translucency of each layer is described below. In the present invention, for example, the L*, a*, b* chromaticity of the L*a*b* color system may be used as a measure of shade. Translucency may be measured by, for example, ΔL* of the L*a*b* color system. These values represent values after sintering when the mill blank is a zirconia pre-sintered body. The measurement methods will be described in detail in the EXAMPLES section below.

In the enamel layer (2), the chromaticity in the L*a*b* color system is preferably L*=68 to 90, a*=−3 to 5, b*=0 to 24, more preferably L*=70 to 82, a*=−2 to 4, b*=2 to 23.

The translucency ΔL* of the enamel layer (2) is preferably 4 to 20, more preferably 7 to 18, even more preferably 8 to 16. With the translucency falling in these ranges, the mill blank portion can have even superior aesthetics.

The shade of the first portion (4) is not particularly limited. However, in view of preventing the prosthesis from developing an overly strong color from inside that makes the dental mill blank unnaturally dark as a prosthetic crown, it is preferable that the first portion (4) have a shade that falls between the shade of the enamel layer and the shade of dentin. In the first portion (4), the chromaticity in the L*a*b* color system is preferably L*=62 to 86, a*=−2 to 7, b*=4 to 27, more preferably L*=64 to 85, a*=−1 to 6, b*=6 to 23, even more preferably L*=64 to 85, a*=−1 to 4, b*=6 to 23.

The translucency ΔL* of the first portion (4) is preferably 4 to 18, more preferably 5 to 17, even more preferably 6 to 11. With the translucency falling in these ranges, the second portion (5) can appear in a moderate shade.

In the second portion (5), the chromaticity in the L*a*b* color system is preferably L*=60 to 85, a*=−2 to 7, b*=4 to 28, more preferably L*=63 to 83, a*=−1 to 6, b*=7 to 26, even more preferably L*=63 to 83, a*=−1 to 4, b*=7 to 26.

The translucency ΔL* of the second portion (5) is preferably 2 to 13, more preferably 2 to 10, even more preferably 3 to 7. With the translucency falling in these ranges, the color masking effect improves, and a shade comparable to the shade of natural teeth can be produced.

When the second portion (5) has a two-layer construction, the chromaticity in the L*a*b* color system is preferably L*=62 to 85, a*=−2 to 7, b*=4 to 28, more preferably L*=63 to 83, a*=−1 to 6, b*=7 to 26 in the upper layer (9) of the second portion (5). In the lower layer (10) of the second portion (5), the chromaticity in the L*a*b* color system is preferably L*=60 to 83, a*=−1 to 7, b*=6 to 28, more preferably L*=60 to 80, a*=0 to 7, b*=8 to 28.

The upper layer (9) of the second portion (5) has a translucency ΔL* of preferably 2 to 13, more preferably 2 to 10, even more preferably 3 to 7. The lower layer (10) of the second portion (5) has a translucency ΔL* of preferably 2 to 10, more preferably 2 to 8, even more preferably 3 to 6. With the translucency falling in these ranges, the mill blank portion shows a gradual color masking effect, and can accommodate more than one shade by changing the dental cap position as desired when fabricating a dental cap.

In view of producing a more natural appearance close to natural teeth, it is preferable in a mill blank portion of the present invention that the adjacent layers in the layered structure have different shades and/or different translucencies. For example, in an embodiment in which the first portion (4) and the second portion (5) have the same shade, it is preferable in view of a more natural appearance that the mill blank portion have translucencies satisfying the relationship that translucency ΔL* of core layer (3)<translucency ΔL* of enamel layer (2). In such an embodiment, the difference between the translucency ΔL* of enamel layer (2) and the translucency ΔL* of core layer (3) is preferably 1 to 9, more preferably 2 to 8, even more preferably 3 to 7. In view of a more natural appearance, it is preferable in the embodiment that the mill blank portion satisfy the following relationships:

L* value of core layer (3)<L* value of enamel layer (2),
a* value of enamel layer (2)<a* of core layer (3), and
b* value of enamel layer (2)<b* value of core layer (3).

In an embodiment in which the first portion (4) and the second portion (5) have different shades, it is preferable in view of a more natural appearance that the mill blank portion have translucencies satisfying the relationship that translucency ΔL* of second portion (5)<translucency ΔL* of first portion (4)<translucency ΔL* of enamel layer (2). In such an embodiment, the difference between the translucency ΔL* of enamel layer (2) and the translucency ΔL* of first portion (4) is preferably 1 to 9, more preferably 2 to 8, even more preferably 3 to 7. The difference between the translucency ΔL* of first portion (4) and the translucency ΔL* of second portion (5) is preferably 1 to 9, more preferably 2 to 8, even more preferably 3 to 6. In view of a more natural appearance, it is preferable in the embodiment that the mill blank portion satisfy the following relationships:

L* value of first portion (4)<L* value of enamel layer (2),
a* value of enamel layer (2)<a* value of first portion (4), and
b* value of enamel layer (2)<b* value of first portion (4).

In view of a more natural appearance, it is preferable in the embodiment that the mill blank portion satisfy the following relationships:

L* value of second portion (5)<L* value of first portion (4),
a* value of first portion (4)<a* value of second portion (5), and
b* value of first portion (4)<b* value of second portion (5).

In an embodiment in which the second portion (5) has a two-layer construction, it is preferable in view of a more natural appearance that the mill blank portion have translucencies satisfying the relationship that translucency ΔL* of the lower layer (10) of second portion (5)<translucency ΔL* of the upper layer (9) of second portion (5)<translucency ΔL* of first portion (4)<translucency ΔL* of enamel layer (2). In such an embodiment, the difference between the translucency ΔL* of enamel layer (2) and the translucency ΔL* of first portion (4) is preferably 1 to 9, more preferably 2 to 8, even more preferably 3 to 7. The difference between the translucency ΔL* of first portion (4) and the translucency ΔL* of the upper layer (9) of second portion (5) is preferably 1 to 7, more preferably 1 to 6, even more preferably 2 to 5. The difference between the translucency ΔL* of the upper layer (9) of second portion (5) and the translucency ΔL* of the lower layer (10) of second portion (5) is preferably 1 to 7, more preferably 1 to 6, even more preferably 2 to 5. In view of a more natural appearance, it is preferable in the embodiment that the mill blank portion satisfy the following relationships:

L* value of first portion (4)<L* value of enamel layer (2),
a* value of enamel layer (2)<a* value of first portion (4), and
b* value of enamel layer (2)<b* value of first portion (4).

In view of a more natural appearance, it is preferable in the foregoing embodiment that the mill blank portion satisfy the following relationships:

L* value of the lower layer (10) of second portion (5)<L* value of the upper layer (9) of second portion (5)<L* value of first portion (4),
a* value of first portion (4)<a* value of the upper layer (9) of second portion (5)<a* value of the lower layer (10) of second portion (5),
b* value of first portion (4)<b* value of the upper layer (9) of second portion (5)<b* value of the lower layer (10) of second portion (5).

In view of a more natural appearance, it is preferable in the foregoing embodiment that the mill blank portion satisfy the following relationships:

L* value of the lower layer (10) of second portion (5)<L* value of the upper layer (9) of second portion (5)<L* value of first portion (4)<L* value of enamel layer (2),
a* value of enamel layer (2)<a* value of first portion (4)<a* value of the upper layer (9) of second portion (5)<a* of the lower layer (10) of second portion (5), and
b* value of enamel layer (2)<b* value of first portion (4)<b* value of the upper layer (9) of second portion (5)<b* value of the lower layer (10) of second portion (5).

In an embodiment in which the second portion (5) has a two-layer construction, the difference between the shade of the upper layer and the shade of the lower layer is not particularly limited, as long as the present invention can produce its effects. However, for example, when the (L*, a*, b*) of the upper layer (9) of second portion (5) are (L9,a9,b9), and the (L*,a*,b*) of the lower layer (10) of second portion (5) are (L10, a10,b10), the shade difference between these two layers is preferably 0.5 or more, more preferably 1.0 or more, even more preferably 1.5 or more in terms of a value of ΔE calculated according to the following mathematical formula (1).

$$\Delta E=\sqrt{(L10-L9)^2+(a10-a9)^2+(b10-b9)^2} \quad \text{[Math. 1]}$$

A mill blank portion of the present invention may comprise ceramics such as zirconia and glass, or may comprise resin. However, in view of strength and durability, a mill blank portion of the present invention preferably comprises zirconia. In view of workability, a mill blank portion of the present invention is more preferably a zirconia pre-sintered body.

Preferably, the zirconia pre-sintered body comprises a pigment and an additive, in order to satisfy the shade and translucency suited for the layers described above.

The pigment may be, for example, a known pigment used for dental compositions (e.g., inorganic pigments, complex pigments, fluorescent pigments). Examples of the inorganic pigments include oxides such as nickel oxide (NiO), red iron oxide, chromium oxide ($Cr_2O_3$), aluminum oxide ($Al_2O_3$), and titanium oxide. Examples of the complex pigments include $(Zr,V)O_2$, $Fe(Fe,Cr)_2O_4$, $(Ni,Co,Fe)(Fe,Cr)_2O_4 \cdot ZrSiO_4$, and $(Co,Zn)Al_2O_4$. Examples of the fluorescent pigments include $Y_2SiO_5$:Ce, $Y_2SiO_5$:Tb, $(Y,Gd,Eu)BO_3$, $Y_2O_3$:Eu, YAG:Ce, $ZnGa_2O_4$:Zn, and $BaMgAl_{10}O_{17}$:Eu.

Preferably, the zirconia pre-sintered body comprises a stabilizer because the zirconia pre-sintered body, as a dental product, requires the levels of chipping resistance, crack resistance, and bend strength sufficient to withstand repeated mastication. Specifically, it is preferable to add a stabilizer to zirconia before sintering. In this way, a zirconia sintered body, which turns into the base material of a dental product after sintering, can have a matrix phase that is at least one of partially stabilized zirconia and fully stabilized zirconia. In the zirconia sintered body, the primary crystalline phase of zirconia is at least one of tetragonal crystal and cubical crystal. The primary crystalline phase of zirconia may comprise both tetragonal crystal and cubical crystal. Preferably, the zirconia sintered body is essentially free of monoclinic crystals. Here, "essentially free of monoclinic crystals" means that the zirconia sintered body has a monoclinic crystal content of less than 5.0 mass %, preferably less than 1.0 mass %. As is known, partially stabilized zirconia (PSZ) refers to zirconia that is partially stabilized by addition of a stabilizer, and fully stabilized zirconia refers to zirconia fully stabilized with a stabilizer.

Preferably, the stabilizer is at least one oxide selected from the group consisting of yttrium oxide ($Y_2O_3$; hereinafter, "yttria"), titanium oxide ($TiO_2$), calcium oxide (calcia; CaO), magnesium oxide (magnesia; MgO), cerium oxide (ceria; $CeO_2$), aluminum oxide (alumina; $Al_2O_3$), scandium oxide ($Sc_2O_3$), niobium oxide ($Nb_2O_5$), lanthanum oxide ($La_2O_3$), erbium oxide ($Er_2O_3$), praseodymium oxide ($Pr_6O_{11}$), samarium oxide ($Sm_2O_3$), europium oxide ($Eu_2O_3$), and thulium oxide ($Tm_2O_3$). In view of high translucency and improved strength, the stabilizer is preferably yttria. These may be used alone, or two or more thereof may be used in combination.

When the stabilizer is containing yttria, the yttria content is preferably 2 to 8 mol %, more preferably 3 to 6 mol % of total 100 mol % of zirconia and stabilizer. With these yttria contents, it is possible to inhibit a phase transformation to monoclinic crystals, and increase the transparency of the zirconia sintered body.

When calcium oxide is contained as a stabilizer, the calcium oxide content is preferably 2 to 15 mol %, more preferably 2.1 to 12 mol % of total 100 mol % of zirconia and stabilizer.

When magnesium oxide is contained as a stabilizer, the magnesium oxide content is preferably 2 to 12 mol %, more preferably 2.1 to 10 mol % of total 100 mol % of zirconia and stabilizer.

When cerium oxide is contained as a stabilizer, the cerium oxide content is preferably 2 to 18 mol %, more preferably 2.1 to 12 mol % of total 100 mol % of zirconia and stabilizer.

When scandium oxide is contained as a stabilizer, the scandium oxide content is preferably 0.1 to 1 mol %, more preferably 0.1 to 0.3 mol % of total 100 mol % of zirconia and stabilizer.

When lanthanum oxide is contained as a stabilizer, the lanthanum oxide content is preferably 1 to 10 mol %, more preferably 2 to 7 mol % of total 100 mol % of zirconia and stabilizer.

When erbium oxide is contained as a stabilizer, the erbium oxide content is preferably 0.1 to 1 mol %, more preferably 0.1 to 0.3 mol % of total 100 mol % of zirconia and stabilizer.

When praseodymium oxide is contained as a stabilizer, the praseodymium oxide content is preferably 0.1 to 1 mol %, more preferably 0.1 to 0.3 mol % of total 100 mol % of zirconia and stabilizer.

When samarium oxide is contained as a stabilizer, the samarium oxide content is preferably 0.1 to 1 mol %, more preferably 0.1 to 0.3 mol % of total 100 mol % of zirconia and stabilizer.

When europium oxide is contained as a stabilizer, the europium oxide content is preferably 0.1 to 1 mol %, more preferably 0.1 to 0.3 mol % of total 100 mol % of zirconia and stabilizer.

When thulium oxide is contained as a stabilizer, the thulium oxide content is preferably 0.1 to 1 mol %, more preferably 0.1 to 0.3 mol % of total 100 mol % of zirconia and stabilizer.

The content of the stabilizer in the zirconia sintered body can be measured using techniques, for example, such as inductively coupled plasma (ICP) emission spectral analysis, and x-ray fluorescence analysis.

The following describes a method for producing a dental mill blank of the present invention.

A method for producing a dental mill blank of the present invention comprises pre-forming of a core layer (3) by powder pressing, and main pressing of the pre-formed compact of the core layer (3) with an enamel layer (2) covering the core layer (3).

Here, the powder pressing is a method by which a powder for forming a layer of interest (for example, a zirconia powder in the case of the core layer (3)), and a powder containing components such as pigments and additives are prepared, and pressed in a die with a punch.

In pre-forming, the pressure may be applied by following known conditions. However, the pressure needs to be lower than the pressure of the subsequent main pressing. The density of the compact (mill blank portion) obtained is preferably 2.0 to 4.0 $g/cm^3$. The devices and conditions used for main pressing are not limited, as long as the density falls in this range.

When the core layer (3) comprises a second portion (5), it is preferable in the present invention that the method comprises pre-forming of the first portion (4) and second portion (5) by powder pressing, and main pressing of the pre-formed compact of first portion (4) and second portion (5) with an enamel layer (2) covering the compact. More preferably, the method comprises pre-forming of a second portion (5) by powder pressing, disposing a raw material powder of first portion (4) on the second portion (5), pre-forming the first portion (4) and second portion (5) by pressing, and main pressing of the pre-formed compact of first portion (4) and second portion (5) with an enamel layer (2) covering the compact.

The pressure for the pre-forming of the second portion (5) is preferably lower than the pressure for the pre-forming of the first portion (4), and the pressure for the pre-forming of the first portion (4) is preferably lower than the pressure of the subsequent main pressing.

The density of the compact (mill blank portion) obtained is preferably 2.0 to 4.0 $g/cm^3$. The devices and conditions used for main pressing are not limited, as long as the density falls in this range.

In a mill blank portion of the present invention, a core layer (3) of a specific shape can be obtained by pressing and pre-forming the core layer (3) with a die having the specific shape, or by grinding a pre-formed compact of core layer (3) into the specific shape after pressing the core layer (3) with an ordinary die. Preferably, the method for producing a dental mill blank of the present invention comprises molding the first portion (4) and/or second portion (5) into the predetermined shape. Preferably, the pre-formed compact of first portion (4) and second portion (5) having the desired shape is sand blasted before main pressing because sand blasting of the pre-formed compact has the effect to blur the layer boundaries.

Dental Mill Blank

A dental mill blank of the present invention comprises the mill blank portion, preferably with a support unit. The dental mill blank can be secured to a milling machine with the support unit. The method used to attach the support unit to the mill blank portion is not particularly limited. For example, an adhesive may be used to bond the mill blank portion and the support unit to each other.

A dental mill blank of the present invention has dental use, and can be suitably used for, for example, milling for fabrication of dental prostheses such as inlays, onlays, veneers, crowns, bridges, abutment teeth, dental posts, dentures, denture bases, and implant parts (fixtures, abutments) using a dental CAD/CAM system. A method for the production of a dental prosthesis from a dental mill blank of the present invention is not particularly limited, and a known method may be used as appropriate. It is, however, preferable that the method comprises milling of the mill blank.

The present invention encompasses combinations of the foregoing features, provided that such combinations made in various forms within the technical idea of the present invention can produce the effects of the present invention.

EXAMPLES

The following describes the present invention in greater detail by way of Examples. It should be noted, however, that the present invention is in no way limited by the following Examples, and various changes may be made by a person with ordinary skill in the art within the technical idea of the present invention.

Example 1

A zirconia powder was prepared that contained 6 mol % yttria as a stabilizer. The zirconia powder was filled into a cylindrical die of about 11 mm diameter with pigments in such an amount that the second portion (5) had a height of 7.25 mm after pressing. The pigments were used in the amounts shown in Table 1. For pre-forming, the zirconia powder was pressed at 3 kN, and the same amount of zirconia powder was laid on the pre-formed second portion (5) with pigments used in the same amounts. These were then pressed into a pre-formed compact. The pre-formed compact was shaved into a shape of the structure depicted in FIG. 4D as a cross section taken at the second imaginary cutting plane (7) shown in FIG. 1A. This produced a pre-formed compact of core layer (3). The pre-formed compact of core layer (3) was then placed in an 18.4 mm×20.3 mm quadrangular prism-shaped die, and the same zirconia powder used for the first portion (4) and second portion (5) was laid around the pre-formed compact of core layer (3) including first portion (4) and second portion (5). Here, the zirconia powder was added as the raw material of enamel in such an amount that the enamel layer (2) had a height (maximum height) of 18 mm after pressing, together with the pigments added in different combinations and different amounts as shown in Table 1. This was followed by main pressing of the zirconia powder at 75 kN. The mill blank portion was then fired at 1,025° C. for 2 hours using a furnace (Noritake KATANA® F-1, manufactured by SK medical electronics Co., Ltd.). The mill blank portion, fabricated from the zirconia pre-sintered body, had the structure depicted in FIG. 4D as a cross section taken at the second imaginary cutting plane (7) shown in FIG. 1A.

The following describes a method of fabrication of a zirconia sintered body frame. A molding material, or an impression material as it is also called, was used to take a negative imprint of an abutment tooth and its opposing tooth and surrounding dentition. A plaster was poured into the imprint to fabricate a positive plaster cast, in order to reproduce the abutment tooth and its opposing tooth and surrounding dentition. Thereafter, a wax was used to form a wax crown on the abutment tooth of the plaster cast, with adjusted occlusion, shape, and dimensions. The wax crown serves as the base of frame formation. This was followed by taking an optical scan of the abutment tooth and wax crown of the plaster cast with a KATANA® dental scanner D750 (manufactured by Kuraray Noritake Dental Inc.) to obtain three-dimensional digital data of the abutment tooth and wax crown. Instead of taking an optical scan of the plaster cast as in this example, an intraoral scanner may be used to directly take an intraoral optical scan. Instead of using a wax crown, three-dimensional data based on a virtual frame shape may be created using three-dimensional CAD software after taking an optical scan of the plaster cast.

By using the three-dimensional data, the mill blank portion fabricated from the zirconia pre-sintered body was shaped into a front tooth frame with carbide drills (Ø=2.0 mm, Ø=0.8 mm), using a milling machine DWX-50N manufactured by Kuraray Noritake Dental Inc. The mill blank portion was then sintered at 1,550° C. for 2 hours to produce a front tooth frame comprising the zirconia sintered body, using a firing furnace Noritake KATANA® F-1 manufactured by SK medical electronics Co., Ltd.

The excess material on surfaces of the front tooth frame was removed with an electric machining tool coupled to diamond abrasive grains with a shaft. This was followed by sandblasting of the front tooth frame with 50 μm alumina under 0.2 MPa pressure to provide matte surfaces. The surfaces of the front tooth frame were then polished to gloss with PearlSurface® (manufactured by Kuraray Noritake Dental Inc.) to obtain a dental prosthesis of the present invention.

Example 2

A mill blank portion was fabricated, and a dental prosthesis of the present invention was obtained in the same manner as in Example 1, except that the pigments used for the fabrication of the layers were used in the amounts shown in Table 1 to provide different shades for the first portion (4) and the second portion (5).

Example 3

A mill blank portion was fabricated, and a dental prosthesis of the present invention was obtained in the same manner as in Example 1, except that the pigments used for the fabrication of the layers were used in the amounts shown in Table 1 to provide different shades for the first portion (4) and the upper and lower layers of the second portion (5). For fabrication of a pre-formed compact, the zirconia powder, added with the pigments used in the amounts shown in Table 1, was pressed at 3 kN so that the lower layer (10) of the second portion (5) had a height of 4 mm after pressing, and the zirconia powder, separately added for upper layer (9) with the pigments used in the amounts shown in Table 1, was pressed at 3 kN so that the upper layer (9) of the second portion (5) had a height of 3.25 mm after pressing. The upper layer and lower layer of the second portion (5) had a shade difference ΔE of 2.3.

Comparative Example 1

A commercially available zirconia disc UTML A3 (Noritake KATANA® Zirconia, manufactured by Kuraray Noritake Dental Inc.; measuring 98.5 mm×14.0 mm) was prepared as a raw material of a frame. This product has a multilayer structure with four parallel layers, and, unlike the core layer (3), the side face does not have a portion perpendicular to the base. By using the three-dimensional data obtained in Example 1, the zirconia disc was shaped into a frame with carbide drills (Ø=2.0 mm, Ø=0.8 mm), using a milling machine DWX-50N manufactured by Kuraray Noritake Dental Inc. The frame, as a precursor, was then sintered at 1,550° C. for 2 hours to produce a front tooth frame, using a firing furnace Noritake KATANA® F-1 manufactured by SK medical electronics Co., Ltd.

The excess material on surfaces of the front tooth frame were removed with an electric machining tool coupled to diamond abrasive grains with a shaft. This was followed by sandblasting of the front tooth frame with 50 μm alumina under 0.2 MPa pressure to provide matte surfaces. The surfaces of the front tooth frame were then polished to gloss with PearlSurface® (manufactured by Kuraray Noritake Dental Inc.) to obtain a dental prosthesis.

Comparative Example 2

Figure 5A:
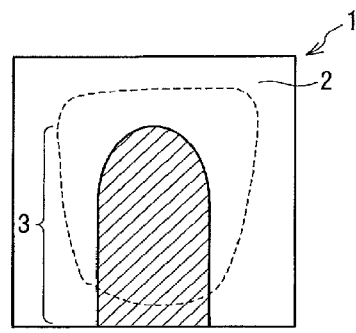
FIG. 5A is a cross sectional view of a mill blank portion according to Comparative Example 2 at a second imaginary cutting plane.

A mill blank portion was fabricated, and a dental prosthesis was obtained in the same manner as in Example 1, except that the pigments used for the fabrication of the layers were used in the amounts shown in Table 1, and that the pre-formed compact of body layer was shaved into the shape of the core layer (3) depicted in FIG. 5A.

Comparative Examples 3 and 4

Figure 5B:
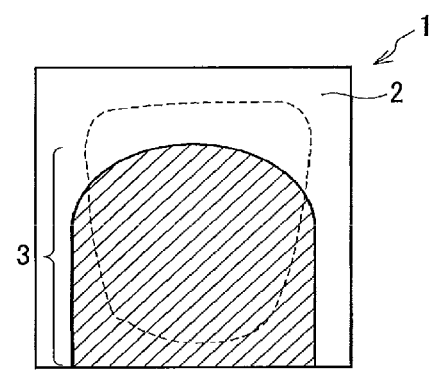
FIG. 5B is a cross sectional view of a mill blank portion according to Comparative Example 3 at a second imaginary cutting plane.
Figure 5C:
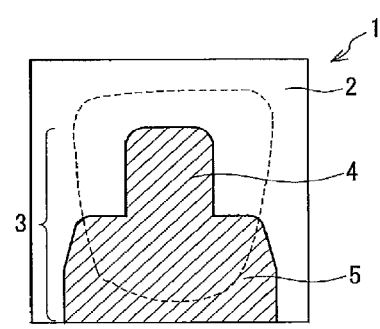
FIG. 5C is a cross sectional view of a mill blank portion according to Comparative Example 4 at a second imaginary cutting plane.

A mill blank portion was fabricated, and a dental prosthesis was obtained in the same manner as in Example 1, except that the pre-formed compact of body layer was shaved into the shapes of the core layers (3) depicted in FIG. 5B and FIG. 5C.

Measurement of Shade

The zirconia powder used for each layer of the dental prostheses fabricated in Examples and Comparative Examples was used by itself to fabricate a monolayer zirconia sintered body, and the zirconia sintered body was worked into a circular disc measuring 14 mm in diameter and 1.2 mm in thickness (the both surfaces were polished with #600 paper) to prepare a specimen (n=1). The specimen was measured for chromaticity against white background, in line with the L*a*b* color system (JIS Z 8781-4:2013 Color Measurements—Part 4: CIE 1976 L*a*b* color space), using a spectrophotometer CM-3610A (manufactured by Konica Minolta Inc.) under predetermined measurement conditions (D65 illuminant, measurement mode: SCI, an area ratio of measurement area to illumination area=8 mm:11 mm in diameter). Here, "white background" means the white part of the hiding-power test paper described in Part 4, Section 1 of JIS K 5600-4-1:1999.

Measurement of Translucency

The zirconia powder used for each layer of the dental prostheses fabricated in Examples and Comparative Examples was used by itself to fabricate a monolayer zirconia sintered body, and the zirconia sintered body was worked into a circular disc measuring 14 mm in diameter and 1.2 mm in thickness (the both surfaces were polished with #2000 paper) to prepare a specimen (n=1). The specimen was measured for L* values of lightness (color space) of the L*a*b* color system (JIS Z 8781-4:2013) using a spectrophotometer CM-3610A (manufactured by Konica Minolta Inc.) under predetermined measurement conditions (D65 illuminant, geometric condition c (di:8°, de:8°), diffused illumination: 8° viewing, measurement mode: SCI, an area ratio of measurement area to illumination area=8 mm:11 mm in diameter). The measured values were then used to calculate a value that indicates translucency, as follows. The L* value measured for a specimen against white background was used as a first L* value, and the same specimen was measured for a second L* value against black background. The second L* value was then subtracted from the first L* value to derive a value (ΔL*) as an index of translucency. Here, "white background" means the white part of the hiding-power test paper described in Part 4, Section 1 of JIS K 5600-4-1:1999, and "black background" means the black part of the hiding-power test paper.

Visual Evaluation

The dental prosthesis fabricated in each Example and Comparative Example (n=1) was visually compared with shade A3 of the VITA shade guide. The following criteria were used for determination.

A: The shade was comparable to the VITA shade, and the aesthetic quality was most desirable. The dental prosthesis also had a structure that most resembled the structure of natural tooth.

B: The shade was close to the VITA shade, and the aesthetic quality was desirable. The dental prosthesis also had a structure that most resembled the structure of natural tooth.

C: The shade was close to the VITA shade, and the aesthetic quality was desirable. The structure resembled the structure of natural tooth.

D: The shade was close to the VITA shade, and the aesthetic quality was desirable. However, the structure differed from the structure of natural tooth.

E: The shade did not match the VITA shade, and the aesthetic quality was poor. The structure differed from the structure of natural tooth.

TABLE 1

| | | Amount of pigment added[1] | | | | Shade | | | Translucency | Evaluation Visual |
|---|---|---|---|---|---|---|---|---|---|---|
| | | NiO | (Zr,V)O$_2$ | Cr$_2$O$_3$ | Al$_2$O$_3$ | L* | a* | b* | ΔL* | inspection |
| Example 1 | Enamel | 0.009 | 0.014 | 0.0004 | 0 | 79.93 | −0.34 | 17.77 | 9 | B |
| | First portion | — | — | — | — | — | — | — | — | |
| | Second portion | 0.029 | 0.045 | 0 | 0 | 75.60 | 3.18 | 22.18 | 5 | |
| Example 2 | Enamel | 0.009 | 0.014 | 0.0004 | 0 | 79.93 | −0.34 | 17.77 | 9 | A |
| | First portion | 0.021 | 0.032 | 0 | 0 | 78.11 | 1.51 | 20.99 | 6 | |
| | Second portion | 0.029 | 0.045 | 0 | 0 | 75.6 | 3.18 | 22.18 | 5 | |
| Example 3 | Enamel | 0.009 | 0.014 | 0.0004 | 0 | 79.93 | −0.34 | 17.77 | 9 | A |
| | First portion | 0.021 | 0.032 | 0 | 0 | 78.11 | 1.51 | 20.99 | 6 | |
| | Upper layer of second portion | 0.029 | 0.045 | 0 | 0 | 75.60 | 3.18 | 22.18 | 5 | |
| | Lower layer of second portion | 0.035 | 0.055 | 0 | 0 | 73.80 | 4.21 | 23.15 | 4 | |
| Comparative Example 1 | Enamel | — | — | — | — | 82.47 | 0.10 | 16.36 | 10 | D |
| | Intermediate layer 1 | — | — | — | — | 80.58 | 1.53 | 17.87 | 7 | |
| | Intermediate layer 2 | — | — | — | — | 78.42 | 3.21 | 19.76 | 6 | |
| | Body | — | — | — | — | 77.48 | 3.95 | 18.77 | 5 | |

TABLE 1-continued

| | | Amount of pigment added[1] | | | | Shade | | | Translucency | Evaluation Visual |
|---|---|---|---|---|---|---|---|---|---|---|
| | | NiO | (Zr,V)O$_2$ | Cr$_2$O$_3$ | Al$_2$O$_3$ | L* | a* | b* | ΔL* | inspection |
| Comparative Example 2 | Enamel | 0.011 | 0.018 | 0.0005 | 0 | 70.85 | −1.25 | 14.20 | 9 | C |
| | Intermediate layer | — | — | — | — | — | — | — | — | |
| | Body | 0.029 | 0.045 | 0 | 0.5 | 71.48 | 0.35 | 23.67 | 4 | |

[1]Content of each pigment relative to total amount of zirconia powder and all pigments (mass %).

Visual evaluations confirmed that, because of the shape similar to the layered structure of natural tooth, the front tooth frames fabricated as the dental prostheses of Examples 1 to 3 had an appearance close to natural teeth, and were aesthetically more desirable than the dental prosthesis of Comparative Example 1 fabricated from a mill blank portion having a layered structure with four parallel layers. The dental prosthesis of Comparative Example 2 had an appearance close to the structure of natural tooth. However, the front tooth frames fabricated as the dental prostheses of Examples 1 to 3 had an appearance visually even closer to natural teeth, and were aesthetically more desirable than the dental prosthesis of Comparative Example 2 fabricated from a shell-shaped mill blank portion, particularly in terms of transparency at the incisal edge portion. Visual inspection of the dental prostheses of Comparative Examples 3 and 4 confirmed that the portion corresponding to dentin was narrower than that observed in the dental prostheses of Examples 1 to 3, and the dental prostheses of Comparative Examples 3 and 4 were aesthetically inferior in terms of this and other qualities.

INDUSTRIAL APPLICABILITY

A dental mill blank of the present invention can be used as a dental prosthesis of high aesthetic quality.

REFERENCE SIGNS LIST

1 Mill blank portion
2 Enamel layer
3 Core layer
4 First portion
5 Second portion
51 Pedestal face
6 First imaginary cutting plane
7 Second imaginary cutting plane
8 Third portion
9 Upper layer of second portion
10 Lower layer of second portion

The invention claimed is:

1. A dental mill blank that comprises a mill blank portion having a layered structure of two or more layers, and in which the layered structure comprises an enamel layer and a core layer,
the core layer comprising a first portion that is substantially a frustum,
the frustum having a side face forming a part of an interface between the enamel layer and the core layer,
wherein the core layer further comprises a second portion joined to the first portion at a relatively wider base B of the frustum, and
wherein the core layer is shaped to include a step formed by the first portion and the second portion.

2. The dental mill blank according to claim 1, wherein an angle θ1 created by the side face of the frustum and an imaginary line orthogonal to the relatively wider base B of the frustum falls in a range of 0° to 80° (excluding 0°) on an imaginary plane orthogonal to the base B.

3. The dental mill blank of claim 1, wherein the frustum has a circular or elliptical base.

4. The dental mill blank according to claim 1, wherein the second portion has a pedestal face that is in contact with the base B of the first portion, and the pedestal face forms a part of the interface around a region contacting the first portion.

5. The dental mill blank according to claim 4, wherein the second portion is a portion that is
a) substantially a frustum having the pedestal face as a relatively narrower base C,
b) substantially a column having the pedestal face as a base C, or
c) a combination of a portion that is substantially a frustum having the pedestal face as a relatively narrower base C, and a portion that is substantially a column joined to a relatively wider base of the frustum.

6. The dental mill blank according to claim 5, wherein the second portion is a cylindrical portion having the pedestal face as a base C.

7. The dental mill blank of claim 1, wherein the second portion comprises a plurality of layers of different shades.

8. The dental mill blank according to claim 7, wherein the second portion comprises and a lower layer that are different in shade, the upper layer and the lower layer having a shade difference ΔE of 0.5 or more as calculated by the following formula, $$\Delta E = \sqrt{(L10-L9)^2 + (a10-a9)^2 + (b10-b9)^2}$$ [Math. 1]

where (L9,a9,b9) represent (L*,a*,b*) of the upper layer of the second portion, and (L10,a10,b10) represent (L*,a*,b*) of the lower layer of the second portion.

9. The dental mill blank of claim 1, wherein the first portion has chromaticity with L*=62 to 86, a*=−2 to 7, and b*=4 to 27 in the L*a*b* color system.

10. The dental mill blank of claim 1, wherein the core layer further comprises a third portion joined to the first portion at a relatively narrower base A of the frustum forming the first portion, and/or the base A of the core layer forms a part of the interface between the enamel layer and the core layer.

11. The dental mill blank of claim 1, wherein the mill blank portion is a zirconia pre-sintered body.

12. A dental prosthesis comprising a dental mill blank of claim 1.

13. A dental mill blank that comprises a mill blank portion having a layered structure of two or more layers, and in which the layered structure comprises an enamel layer and a core layer,
the core layer comprising a first portion that is substantially a frustum, the frustum having a side face forming a part of an interface between the enamel layer and the core layer, wherein the core layer further comprises a second portion joined to the first portion at a relatively wider base B of the frustum, and wherein the second portion is a portion that is d) substantially a frustum having a relatively narrower base C representing a surface identical in size and position to the base B, e) substantially a column having a base C representing a surface identical in size and position to the base B, or f) a combination of a portion that is substantially a frustum having a relatively narrower base C representing a surface identical in size and position to the base B of the first portion, and a portion that is substantially a column having a base E representing a surface identical in size and position to a relatively wider base D of the frustum.

14. The dental mill blank according to claim 13, wherein the second portion is a cylindrical portion having a base C representing a surface identical in size and position to the base B.

\* \* \* \* \*